US009095164B2

(12) United States Patent
Meehan

(10) Patent No.: US 9,095,164 B2
(45) Date of Patent: Aug. 4, 2015

(54) ANIMAL FEED COMPOSITION FOR INCREASED PRODUCTION OF GLUTATHIONE PEROXIDASE AND SUPEROXIDE DISMUTASE

(76) Inventor: Kevin Meehan, Jackson, WY (US)

( * ) Notice: Subject to any disclaimer, the term of this patent is extended or adjusted under 35 U.S.C. 154(b) by 2919 days.

(21) Appl. No.: 11/351,538

(22) Filed: Feb. 9, 2006

(65) Prior Publication Data

US 2006/0177485 A1    Aug. 10, 2006

Related U.S. Application Data

(60) Provisional application No. 60/651,784, filed on Feb. 9, 2005.

(51) Int. Cl.
| | | |
|---|---|---|
| *A23L 1/305* | (2006.01) | |
| *A23K 1/10* | (2006.01) | |
| *A23K 1/14* | (2006.01) | |
| *A23K 1/16* | (2006.01) | |
| *A23K 1/175* | (2006.01) | |
| *A23K 1/18* | (2006.01) | |
| *A23L 1/30* | (2006.01) | |
| *A61K 31/015* | (2006.01) | |
| *A61K 31/198* | (2006.01) | |
| *A61K 33/04* | (2006.01) | |
| *A61K 36/31* | (2006.01) | |

(52) U.S. Cl.
CPC .............. *A23L 1/3051* (2013.01); *A23K 1/10* (2013.01); *A23K 1/14* (2013.01); *A23K 1/1606* (2013.01); *A23K 1/1634* (2013.01); *A23K 1/1758* (2013.01); *A23K 1/18* (2013.01); *A23L 1/3002* (2013.01); *A61K 31/015* (2013.01); *A61K 31/198* (2013.01); *A61K 33/04* (2013.01); *A61K 36/31* (2013.01); *A23V 2002/00* (2013.01)

(58) Field of Classification Search
CPC ...................................... A61K 33/04
USPC ......................................... 424/439
See application file for complete search history.

(56) References Cited

U.S. PATENT DOCUMENTS

| | | | | |
|---|---|---|---|---|
| 5,232,732 | A * | 8/1993 | Harris et al. ................... | 426/589 |
| 5,686,108 | A | 11/1997 | Pusateri et al. ................ | 424/464 |
| 5,770,217 | A | 6/1998 | Kutilek, III et al. ........... | 424/442 |
| 5,882,646 | A | 3/1999 | Pusateri et al. ............. | 424/195.1 |
| 5,897,902 | A * | 4/1999 | Kemp et al. .................... | 426/412 |
| 6,262,019 | B1 | 7/2001 | Keller et al. | |
| 6,361,812 | B1 | 3/2002 | Ekanayake et al. ........... | 426/321 |
| 6,436,450 | B1 | 8/2002 | Omary et al. .................. | 424/755 |
| 6,544,547 | B2 * | 4/2003 | Hageman ....................... | 424/439 |
| 6,558,723 | B2 | 5/2003 | Ekanayake et al. ........... | 426/321 |
| 7,001,610 | B2 | 2/2006 | Stewart | |
| RE39,705 | E | 6/2007 | Keller et al. | |
| 2003/0091518 | A1 | 5/2003 | Pauly et al. ..................... | 424/59 |
| 2003/0185905 | A1 | 10/2003 | Muhlbauer ................... | 424/725 |
| 2003/0211209 | A1 | 11/2003 | Ekanayake et al. ....... | C12H 1/10 |
| 2004/0115309 | A1 | 6/2004 | Harris .............................. | 426/72 |
| 2008/0020035 | A1 | 1/2008 | Prasad et al. | |

FOREIGN PATENT DOCUMENTS

| | | |
|---|---|---|
| JP | 8266256 | 10/1996 |
| WO | WO9805005 A1 | 2/1998 |
| WO | WO0054838 A1 | 9/2000 |

OTHER PUBLICATIONS

Becky (http://www.cyber-kitchen.com/ubbs/archive/POULTRY/Chicken_Chicken_Stuffed_Cabbage_Rolls.html (2002)).*
Marla (http://www.freerecipesbook.com/free-recipe-6686-cabbage-rolls-with-sour-cream-sauce.html.*
Wikipedia (http://web.archive.org/web/20050120174017/http://en.wikipedia.org/wiki/Brown_rice (Jan. 2005)).*
Salt Institute, "Salt and Trace Minerals for Livestock, Poultry and Other Animals; Selenium for Animals," Internet Article, https://www.saltinstitute.org/47t.html, 1974, pp. 1-4.
Midnight Illusions Ltd, "Cysteine & Cystine," The Alternative Health CD, Gold Edition, 2000-2005, pp. 1-4.
BBC News World Edition UK Edition 2005; "Food combining fights cancer, "Internet Article, http:/ne/vs.bbc.co.uk/2/hi/health/290 . . . , pp. 1-2.
Lippincott Williams & Wilkins, "Dietary Phytochemical Delivery: Glucosinolates/Isothiocyanates," Nutrition Today 37(5), Sep./Oct. 2002 (one page).
The World's Healthest Foods, "Cancer Protection," Retrieved from www.whfoods.com/genpage.ph . . . , Sep. 2003 (one page).

* cited by examiner

*Primary Examiner* — Jake Vu
(74) *Attorney, Agent, or Firm* — McGuireWoods LLP

(57) ABSTRACT

A food composition for consumption by mammals is designed to increase the production of glutathione peroxidase and superoxide dismutase. A serving of the food composition has a total weight and includes, in order of decreasing weight, a meat, a *brassica* vegetable, and brown rice.

27 Claims, No Drawings

ANIMAL FEED COMPOSITION FOR INCREASED PRODUCTION OF GLUTATHIONE PEROXIDASE AND SUPEROXIDE DISMUTASE

CROSS REFERENCE TO RELATED APPLICATIONS

This application claims priority from U.S. Provisional Patent Application No. 60/651,784, which was filed on 9 Feb. 2005. U.S. Provisional Patent Application No. 60/651,784 is incorporated by reference in its entirety.

BACKGROUND

1. Technical Field

This disclosure relates generally to a feed composition, and more specifically to an animal feed composition formulated to provide increased production of glutathione peroxidase and superoxide dismutase.

2. Description of the Related Art

The Merriam-Webster Medical Dictionary (2002) defines a carotenoid as any of various usually yellow to red pigments (as carotenes) found widely in plants and animals and characterized chemically by a long aliphatic polyene chain composed of eight isoprene units.

The Merriam-Webster® Medical Dictionary (2002) defines a methionine as a crystalline sulfur-containing essential amino acid $C_5H_{11}NO_2S$ that occurs in the L-form as a constituent of many proteins (as casein and egg albumin), that is important especially as a source of sulfur for the biosynthesis of cysteine and as a source of methyl groups for transmethylation reactions (as in the biosynthesis of choline, creatine, and adrenaline), and that is used as a dietary supplement for human beings and their domestic mammals and poultry and in the treatment of fatty infiltration of the liver.

The Merriam-Webster® Medical Dictionary (2002) defines a cysteine as a sulfur-containing amino acid $C_3H_7NO_2S$ that occurs in many proteins and glutathione and that is readily oxidizable to cystine.

The Merriam-Webster® Medical Dictionary (2002) defines an antioxidant as any of various substances (as beta-carotene, vitamin C, and alpha-tocopherol) that inhibit oxidation or reactions promoted by oxygen and peroxides and that include many held to protect the living body from the deleterious effects of free radicals.

The Merriam-Webster® Medical Dictionary (2002) defines glutathione as a peptide $C_{10}H_{17}N_3O_6S$ that contains one amino acid residue each of glutamic acid, cysteine, and glycine, that occurs widely in plant and animal tissues, and that plays an important role in biological oxidation-reduction processes and as a coenzyme.

The Merriam-Webster® Medical Dictionary (2002) defines peroxidase as an enzyme occurring especially in plants, milk, and white blood cells and consisting of a protein complex with hematin groups that catalyzes the oxidation of various substances by peroxides.

The Merriam-Webster® Medical Dictionary (2002) defines superoxide dismutase as a metal-containing antioxidant enzyme that reduces potentially harmful free radicals of oxygen formed during normal metabolic cell processes to oxygen and hydrogen peroxide—abbreviation SOD.

The Merriam-Webster® Medical Dictionary (2002) defines an international unit as the amount of specific physiological activity of a standardized preparation (as of a vitamin) that is agreed upon as an international standard especially for comparison with other biologicals containing the substance in impure form or with a related biologically active substance; also: the amount of the biologically active substance in the standard amount of the preparation producing this activity.

DETAILED DESCRIPTION

The design of this animal food product contemplates substantial nutrition coupled with a novel formulation which focuses on increasing glutathione peroxidase and superoxide dismutase. The food components that are found in embodiments of the invention provide the proteins required for mammals to achieve this goal as well as the necessary fiber which encourages bowel motility.

According to exemplary embodiments of the invention, the primary ingredients of an animal food product include, in order of decreasing weight, chicken, green cabbage, brown rice, and horseradish. The preferred ratio of these ingredients in these exemplary embodiments is listed below in Table 1, where one pound of chicken is used as a reference. The vitamin, amino acid, and element ratio for the ingredients of Table 1 are listed below in Table 2.

TABLE 1

| |
|---|
| 16 ounces chicken |
| 4½ ounces green cabbage |
| 3 ounces brown rice, short grain |
| ½ ounce horseradish |

TABLE 2

| |
|---|
| 50,000 International Units (IU) mixed carotenoids |
| 500 milligrams (mg) L-methionine |
| 500 mg N-acetyl-L-cysteine |
| 250 micrograms (mcg) sodium selenate (selenium) |

The physiological action of the ingredients listed in Table 2 is described below. Selenium is a major component of glutathione peroxidase, which has been shown to negate superoxide anion free radicals (Oz'). Cysteine and methionine are both sulfur-containing side chain amino acids and influence the concentration of sulfur-containing biological compounds, such as glutathione (the component of glutathione peroxidase).

This formula functions to increase the levels of both glutathione peroxidase and superoxide dismutase, aiding in protection of DNA in mammals, while also providing a low fat diet. That is, the animal food product contains the ingredients listed in Tables 1 and 2 in amounts effective to increase the production of glutathione peroxidase and superoxide dismutase when the animal food product is consumed by mammals.

The mixed carotenoids are antioxidants in general.

Chicken is preferred because its meat or flesh has a relatively low fat concentration, but in alternative embodiments of the invention the flesh of other species of poultry or even other species of animal (e.g., beef, pork, veal) could be used as long as the vitamin, amino-acid, and element ratio of Table 2 is maintained.

It should be noted that maintaining the ratios of Table 2 does not necessarily mean that the ratio of vitamin, amino-acids, and elements listed in Table 2 are strictly held at that specific ratio. Rather, the actual ratio may be more or less than the preferred ratio by about 30% in either direction (30% more than the preferred ratio or 30% less than the preferred ratio) and still achieve the benefits according to embodiments of the invention. Ratios below 30% of the preferred ratio may not give a significant benefit while ratios above 30% of the preferred ratio may actually be harmful, particularly with respect to the methionine.

Consequently, other embodiments of the invention may have more ingredients than those listed in Table 1, but the other embodiments will still have, at the least, the same ratio that is exhibited between the elements of Table 2 relative to the total weight of the ingredients listed in Table 1. In other words, the ratios of carotenoids, sodium selenate, methionine, and cysteine for other embodiments of the invention may be approximately 30% more or less than the preferred ratios that can be calculated from Tables 1 and 2.

The brown rice encourages bowel motility, expediting the removal of unwanted material. Green cabbage and horseradish are both sulfur containing *brassica* family vegetables which increase levels of peroxidase and superoxide dismutase. In alternative embodiments of the invention other *brassica* family vegetables may be used in addition to the green cabbage and horseradish or in place of one or both of the green cabbage and horseradish.

According to some embodiments of the invention, an animal food product may consist only of the four ingredients listed in Table 1.

The invention may be practiced in many ways. What follows are exemplary, non-limiting descriptions of some embodiments of the invention.

According to some embodiments, a serving of a food product for consumption by animals includes carotenoids, methionine, cysteine, and sodium selenate, where the serving of the food product has a total weight.

According to some embodiments, the methione consists of L-methionine, and a ratio (by weight) of methione to the total weight is no less than 500 milligrams per 24 ounces.

According to some embodiments, the cysteine consists of N-acetyl-L-cysteine, and a ratio (by weight) of the cysteine to the total weight is no less than 500 milligrams per 24 ounces.

According to some embodiments, a ratio (by weight) of carotenoids to the total weight is no less than 50,000 IU per 24 ounces.

According to some embodiments, a ratio (by weight) of sodium selenate to the total weight is no less than 250 micrograms per 24 ounces.

According to some embodiments, the serving of the food product further includes chicken, brown rice, and at least one vegetable from the *brassica* family.

According to some embodiments, a ratio (by weight) of the at least one vegetable from the *brassica* family to the total weight is no less than 5:24.

According to some embodiments, the at least one vegetable from the *brassica* family includes green cabbage and horseradish.

According to some embodiments, a ratio (by weight) of green cabbage to the total weight is no less than 4.5:24.

According to some embodiments, a ratio (by weight) of horseradish to the total weight is no less than 0.5:24.

According to some embodiments, a food composition for consumption by mammals is designed to increase the production of glutathione peroxidase and superoxide dismutase, where a serving of the food composition includes, in order of decreasing weight, a meat, a *brassica* vegetable, and brown rice, where the serving of the food composition has a total weight.

According to some embodiments, a ratio (by weight) of the *brassica* vegetable to total weight is no less than 5:24.

According to some embodiments, the *brassica* vegetable includes green cabbage and horseradish.

According to some embodiments, a ratio (by weight) of green cabbage to the total weight is no less than 4.5:24.

According to some embodiments, the meat consists of chicken.

According to some embodiments, the serving further includes carotenoids, methionine, cysteine, and sodium selenate.

According to some embodiments, a ratio of carotenoids to the total weight is no less than 50,000 IU per 24 ounces.

According to some embodiments, a ratio (by weight) of methionine to the total weight is no less than 500 milligrams per 24 ounces.

According to some embodiments, a ratio (by weight) of cysteine to the total weight is no less than 500 milligrams per 24 ounces.

According to some embodiments, a ratio (by weight) of sodium selenate to the total weight is no less than 250 micrograms per 24 ounces.

A person skilled in the art will be able to practice the inventive principles in view of the exemplary embodiments described in this specification, where numerous details have been set forth in order to provide a more thorough understanding of the inventive principles. In some instances, well-known features have not been described in detail in order not to obscure unnecessarily the inventive principles.

Furthermore, having described and illustrated the inventive principles in the exemplary embodiments, it should be apparent that the exemplary embodiments may be modified in arrangement and detail without departing from such principles. I claim all modifications and variations coming within the spirit and scope of the following claims.

The invention claimed is:

1. A food product for consumption by animals, a serving of food product consisting essentially of:
   carotenoids;
   methionine;
   cysteine; and
   selenium, where the serving of the food product has a total weight,
   wherein the food product contains the carotenoids, methionine, cysteine and selenium in amounts effective to increase the production of glutathione peroxidase and superoxide dismutase when the serving of the food product is consumed by the animal.

2. A food product for consumption by animals, a serving of food product comprising:
   carotenoids;
   methionine;
   cysteine; and
   selenium, where the serving of the food product has a total weight,
   the methionine consisting of L-methionine, a ratio (by weight) of methionine to the total weight 500 milligrams per 24 ounces of the serving of food product, plus or minus 30%.

3. The food product of claim 2, wherein the cysteine consists of N-acetyl-L-cysteine, and wherein a ratio (by weight) of the cysteine to the total weight of the serving of food product is 500 milligrams per 24 ounces of the serving of food product, plus or minus 30%.

4. The food product of claim 3, wherein a ratio (by weight) of carotenoids to the total weight of the serving of food product is 50,000 IU per 24 ounces of the serving of food product, plus or minus 30%.

5. The food product of claim 1, the serving comprising:
chicken;
brown rice;
at least one vegetable from the *brassica* family.

6. The food product of claim 5, wherein a ratio (by weight) of the at least one vegetable to the total weight of the serving of food product is approximately 5:24, plus or minus 30%.

7. The food product of claim 5, the at least one vegetable comprising:
green cabbage; and
horseradish.

8. The food product of claim 7, wherein a ratio (by weight) of the green cabbage to the total weight of the serving of food product is approximately 4.5:24, plus or minus 30%.

9. The food product of claim 7, wherein a ratio (by weight) of the horseradish to the total weight of the serving of food product is approximately 0.5:24, plus or minus 30%.

10. A food composition for consumption by mammals, a serving of the food composition comprising, in order of decreasing weight:
a meat;
a *brassica* vegetable; and
brown rice, where the serving of the food composition has a total weight,
wherein the food composition contains the meat, the *brassica* vegetable and the brown rice in amounts effective to increase the production of glutathione peroxidase and superoxide dismutase when a serving of the food composition is consumed by a mammal.

11. The food composition of claim 10, wherein a ratio (by weight) of the *brassica* vegetable to total weight of the food composition is approximately 5:24, plus or minus 30%.

12. The food composition of claim 11, the *brassica* vegetable comprising:
green cabbage; and
horseradish.

13. The food composition of claim 12, wherein a ratio (by weight) of green cabbage to the total weight of the food composition is approximately 4.5:24, plus or minus 30%.

14. The food composition of claim 10, the meat consisting of chicken.

15. The food composition of claim 10, the serving comprising:
carotenoids;
methionine;
cysteine; and
selenium.

16. The food composition of claim 15, wherein a ratio of carotenoids to the total weight of the food composition is approximately 50,000 IU per 24 ounces of the food composition, plus or minus 30%.

17. The food composition of claim 15, wherein a ratio (by weight) of methionine to the total weight of the food composition is approximately 500 milligrams per 24 ounces of the food composition, plus or minus 30%.

18. The food composition of claim 15, wherein a ratio (by weight) of cysteine to the total weight of the food composition is approximately 500 milligrams per 24 ounces of the food composition, plus or minus 30%.

19. The food composition of claim 15, wherein a ratio (by weight) of a compound comprising the selenium to the total weight of the food composition is approximately 250 micrograms per 24 ounces of the food composition, plus or minus 30%.

20. The food product of claim 4, wherein food product comprises sodium selenate, the sodium selenate providing the selenium within the food product.

21. The food product of claim 5, wherein the carotenoids, methionine, cysteine, and the selenium are provided by at least one of the chicken, the brown rice and the at least one vegetable.

22. The food product of claim 5, wherein a weight of the chicken within the serving is greater than a weight of the vegetable within the serving and the weight of the vegetable within the serving is greater than a weight of the brown rice within the serving.

23. A food composition for consumption by mammals, a serving of the food composition consisting of:
chicken;
green cabbage;
short grain brown rice; and
horseradish,
wherein the food composition contains the chicken, the green cabbage, the short grain brown rice and the horseradish in amounts effective to increase the production of glutathione peroxidase and superoxide dismutase when a serving of the food composition is consumed by a mammal.

24. The food composition of claim 23, wherein a weight of the chicken within the serving is greater than a weight of the green cabbage within the serving.

25. The food composition of claim 23, wherein a weight of the green cabbage within the serving is greater than a weight of the short grain brown rice within the serving.

26. The food composition of claim 23, wherein a weight of the short grain brown rice within the serving is greater than a weight of the horseradish within the serving.

27. The food product of claim 20, wherein a ratio (by weight) of the sodium selenate to the total weight of the serving of food product is 250 micrograms per 24 ounces of the serving of food product, plus or minus 30%.

* * * * *